(12) United States Patent
Dotan et al.

(10) Patent No.: US 8,496,580 B2
(45) Date of Patent: Jul. 30, 2013

(54) OMNIDIRECTIONAL AND FORWARD-LOOKING IMAGING DEVICE

(75) Inventors: Gideon Dotan, Yehud (IL); Oz Cabiri, Maccabim (IL); Boaz Shpigelman, Netanya (IL)

(73) Assignee: G.I. View Ltd., Ramat Gan (IL)

( * ) Notice: Subject to any disclaimer, the term of this patent is extended or adjusted under 35 U.S.C. 154(b) by 1120 days.

(21) Appl. No.: 11/596,612

(22) PCT Filed: May 11, 2005

(86) PCT No.: PCT/IL2005/000500
§ 371 (c)(1),
(2), (4) Date: Oct. 29, 2008

(87) PCT Pub. No.: WO2005/110186
PCT Pub. Date: Nov. 24, 2005

(65) Prior Publication Data
US 2009/0082629 A1 Mar. 26, 2009

Related U.S. Application Data

(60) Provisional application No. 60/571,438, filed on May 14, 2004.

(51) Int. Cl.
*A61B 1/06* (2006.01)
*A61B 1/04* (2006.01)

(52) U.S. Cl.
USPC .......................... 600/176; 600/109; 600/160

(58) Field of Classification Search
USPC .................. 600/170, 171, 173, 176; 359/725, 359/726–731
See application file for complete search history.

(56) References Cited

U.S. PATENT DOCUMENTS 3,895,637 A   7/1975   Choy
3,924,625 A   12/1975  Peterson
(Continued)

FOREIGN PATENT DOCUMENTS

DE   3630660   3/1988
EP   0242428   10/1987
(Continued)

OTHER PUBLICATIONS

U.S. Appl. No. 60/571,438.
(Continued)

*Primary Examiner* — Philip R Smith
*Assistant Examiner* — William Chou
(74) *Attorney, Agent, or Firm* — Frommer Lawrence & Haug LLP; William S. Frommer

(57) ABSTRACT

Apparatus including an optical system (20) for use in an endoscope is provided. The optical system has distal and proximal ends, and includes an image sensor (32), positioned at the proximal end of the optical system. The optical system also includes an optical member (34) having distal (36) and proximal ends, and shaped so as to define: (a) a lateral surface, at least a distal portion of which is curved, configured to provide omnidirectional lateral viewing, (b) a distal indentation (44) in the distal end of the optical member, and (c) a proximal indentation (48) in the proximal end of the optical member. The optical system also includes a convex mirror (40), coupled to the distal end of the optical member, and shaped so as define an opening through which the distal indentation passes. A distal lens (52) is positioned distal to the mirror. The optical member, the mirror, and the distal lens have respective rotational shapes about a common rotation axis.

14 Claims, 4 Drawing Sheets

U.S. PATENT DOCUMENTS

| | | |
|---|---|---|
| 4,040,413 A | 8/1977 | Ohshiro |
| 4,066,070 A | 1/1978 | Utsugi |
| 4,077,610 A | 3/1978 | Masuda |
| 4,530,698 A | 7/1985 | Goldstein et al. |
| 4,561,427 A | 12/1985 | Takada |
| 4,566,763 A | 1/1986 | Greguss |
| 4,596,381 A | 6/1986 | Hamrick |
| 4,690,131 A | 9/1987 | Lyddy et al. |
| 4,838,859 A | 6/1989 | Strassmann |
| 4,971,034 A | 11/1990 | Doi et al. |
| 4,976,524 A | 12/1990 | Chiba |
| 5,353,807 A | 10/1994 | DeMarco |
| 5,364,353 A | 11/1994 | Corfitsen et al. |
| 5,395,332 A | 3/1995 | Ressemann et al. |
| 5,398,670 A | 3/1995 | Ortiz et al. |
| 5,471,988 A | 12/1995 | Fujio et al. |
| 5,473,474 A | 12/1995 | Powell |
| 5,509,371 A | 4/1996 | Phillips |
| 5,571,114 A | 11/1996 | Devanaboyina |
| 5,586,968 A | 12/1996 | Grundl et al. |
| 5,604,531 A | 2/1997 | Iddan et al. |
| 5,662,587 A | 9/1997 | Grundfest et al. |
| 5,728,068 A | 3/1998 | Leone et al. |
| 5,745,302 A * | 4/1998 | Ohno .......................... 359/689 |
| 5,863,284 A | 1/1999 | Klein |
| 5,879,325 A | 3/1999 | Lindstrom et al. |
| 5,906,357 A | 5/1999 | Munson, Sr. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |
| 6,130,783 A | 10/2000 | Yagi et al. |
| 6,157,018 A | 12/2000 | Ishiguro et al. |
| 6,315,713 B1 | 11/2001 | Takada |
| 6,332,865 B1 | 12/2001 | Begg et al. |
| 6,333,826 B1 | 12/2001 | Charles |
| 6,341,044 B1 | 1/2002 | Driscoll, Jr. et al. |
| 6,356,296 B1 | 3/2002 | Driscoll, Jr. et al. |
| 6,373,642 B1 | 4/2002 | Wallerstein et al. |
| 6,388,820 B1 | 5/2002 | Wallerstein et al. |
| 6,422,989 B1 | 7/2002 | Hektner |
| 6,424,377 B1 | 7/2002 | Driscoll, Jr. et al. |
| 6,449,103 B1 | 9/2002 | Charles |
| 6,459,451 B2 | 10/2002 | Driscoll, Jr. et al. |
| 6,485,409 B1 | 11/2002 | Voloshin et al. |
| 6,493,032 B1 | 12/2002 | Wallerstein et al. |
| 6,503,192 B1 | 1/2003 | Ouchi |
| 6,517,477 B1 | 2/2003 | Wendlandt |
| 6,527,705 B1 | 3/2003 | Ouchi |
| 6,537,206 B2 | 3/2003 | Takada |
| 6,597,520 B2 | 7/2003 | Wallerstein et al. |
| 6,611,282 B1 | 8/2003 | Trubko et al. |
| 6,646,818 B2 | 11/2003 | Doi |
| 6,648,814 B2 | 11/2003 | Kim et al. |
| 6,682,479 B1 | 1/2004 | Takahashi et al. |
| 6,695,771 B2 | 2/2004 | Takada |
| 6,702,734 B2 | 3/2004 | Kim et al. |
| 6,704,148 B2 | 3/2004 | Kumata |
| 6,709,388 B1 | 3/2004 | Mosse et al. |
| 6,764,441 B2 | 7/2004 | Chiel et al. |
| 6,786,864 B2 | 9/2004 | Matsuura et al. |
| 6,800,056 B2 | 10/2004 | Tartaglia et al. |
| 6,814,728 B2 | 11/2004 | Ouchi |
| 6,824,510 B2 | 11/2004 | Kim et al. |
| 6,827,718 B2 | 12/2004 | Hutchins et al. |
| 6,837,846 B2 | 1/2005 | Jaffe et al. |
| 6,866,626 B2 | 3/2005 | Long et al. |
| 6,869,393 B2 | 3/2005 | Butler |
| 6,911,005 B2 | 6/2005 | Ouchi et al. |
| 6,932,323 B2 | 8/2005 | James |
| 6,974,441 B2 | 12/2005 | Ravo |
| 7,009,782 B2 | 3/2006 | Sekiyama |
| 7,056,283 B2 | 6/2006 | Baror et al. |
| 7,131,740 B2 | 11/2006 | Nishioka |
| 7,154,551 B2 * | 12/2006 | Kuriyama et al. ............ 348/335 |
| 2002/0012059 A1 | 1/2002 | Wallerstein et al. |
| 2002/0109772 A1 | 8/2002 | Kuriyama et al. |
| 2002/0109773 A1 | 8/2002 | Kuriyama et al. |
| 2003/0074015 A1 | 4/2003 | Nakao |
| 2003/0181788 A1 | 9/2003 | Yokoi et al. |
| 2003/0191369 A1 | 10/2003 | Arai et al. |
| 2003/0208219 A1 | 11/2003 | Aznoian et al. |
| 2003/0225433 A1 | 12/2003 | Nakao |
| 2004/0004836 A1 | 1/2004 | Dubuc |
| 2004/0111010 A1 | 6/2004 | Nishiie |
| 2004/0143161 A1 | 7/2004 | Baror et al. |
| 2004/0199087 A1 | 10/2004 | Swain et al. |
| 2004/0199088 A1 | 10/2004 | Bakos et al. |
| 2004/0199196 A1 | 10/2004 | Ravo |
| 2004/0204702 A1 | 10/2004 | Ziegler et al. |
| 2004/0249247 A1 | 12/2004 | Iddan |
| 2004/0254424 A1 * | 12/2004 | Simkulet et al. .............. 600/176 |
| 2004/0260150 A1 | 12/2004 | Bernstein |
| 2005/0038317 A1 | 2/2005 | Ratnakar |
| 2005/0038319 A1 | 2/2005 | Goldwasser et al. |
| 2005/0095200 A1 | 5/2005 | Schwarzberg |
| 2005/0107664 A1 | 5/2005 | Kalloo et al. |
| 2005/0165272 A1 | 7/2005 | Okada et al. |
| 2005/0179805 A1 * | 8/2005 | Avron et al. .................. 348/340 |
| 2006/0152819 A1 * | 7/2006 | Gal et al. ...................... 359/725 |
| 2006/0164733 A1 | 7/2006 | Gal |
| 2006/0238879 A1 | 10/2006 | Togino |
| 2008/0045797 A1 | 2/2008 | Yasushi et al. |
| 2008/0247061 A1 * | 10/2008 | Simkulet et al. .............. 359/730 |
| 2010/0272318 A1 * | 10/2010 | Cabiri et al. .................. 382/106 |

FOREIGN PATENT DOCUMENTS

| | | |
|---|---|---|
| EP | 0267446 | 5/1988 |
| EP | 504413 | 9/1992 |
| EP | 0659387 | 6/1995 |
| EP | 753647 | 1/1997 |
| FR | 1465723 | 3/1967 |
| JP | 5-43114 | 6/1993 |
| JP | 7-313443 | 12/1995 |
| JP | 2000000218235 | 7/2000 |
| JP | 2002341409 | 11/2002 |
| JP | 2006026344 | 2/2006 |
| WO | WO 00/44275 | 8/2000 |
| WO | WO 01/68540 | 9/2001 |
| WO | WO 02/059676 | 8/2002 |
| WO | WO 02/075348 | 9/2002 |
| WO | WO02068035 A1 | 9/2002 |
| WO | WO 03/026272 | 3/2003 |
| WO | WO 03/046830 | 6/2003 |
| WO | WO 03/053225 | 7/2003 |
| WO | WO 2004/008185 | 1/2004 |
| WO | WO 2004/010858 | 2/2004 |
| WO | WO 2004/016299 | 2/2004 |
| WO | WO2004028354 A1 | 4/2004 |
| WO | WO 2006/025045 | 3/2006 |

OTHER PUBLICATIONS

U.S. Appl. No. 60/607,986.
U.S. Appl. No. 60/652,049.

* cited by examiner

OMNIDIRECTIONAL AND FORWARD-LOOKING IMAGING DEVICE

CROSS-REFERENCES TO RELATED APPLICATIONS

The present application claims priority from U.S. Provisional Application 60/571,438, filed May 14, 2004, which is assigned to the assignee of the present application and is incorporated herein by reference.

FIELD OF THE INVENTION

The present invention relates generally to medical devices, and specifically to endoscopic medical devices.

BACKGROUND OF THE INVENTION

Medical endoscopes are used to inspect regions within the body, such as cavities, organs, and joints. Endoscopes typically include a rigid or flexible elongated insertion tube having a set of optical fibers that extend from a proximal handle through the insertion tube to the distal viewing tip of the endoscope. Alternatively, an image sensor, such as a CCD, is positioned near the distal viewing tip. An external or internal light source provides light to the area of interest in the body in the vicinity of the distal tip.

U.S. Pat. No. 5,710,661 to Cook, which is incorporated herein by reference, describes optical apparatus that monitors an entire panorama in low resolution and simultaneously monitors a selected portion of the panorama in high resolution. A mirror having a convex surface of revolution with a hole therein is used as the panoramic portion of the apparatus. The higher resolution part of the apparatus uses a pointing mirror positioned above this hole. The panoramic and higher resolution views are imaged through lenses or optical components onto a detector. The panoramic view is imaged onto the detector as an annulus of light in which either higher or lower elevational angles of the panorama are imaged further away from the detector's center depending upon how the convex mirror is configured. In this way, the resolution of that portion of panorama that is imaged further away from the detector's center is enhanced. The higher resolution view is imaged to the center of the annulus.

U.S. Pat. No. 6,341,044 to Driscoll, Jr. et al., which is incorporated herein by reference, describes a panoramic imaging arrangement comprising a lens block and a system of lenses. The lens block has a substantially vertical axis of revolution and is capable of receiving light from a first, 360 degree surrounding panoramic scene. The system of lenses has a vertical axis of revolution substantially coinciding with the axis of revolution of the lens block, and is positioned to receive light from a second scene which is at least partially located above the first, surrounding panoramic scene.

U.S. Pat. No. 6,493,032 and US Patent Application Publication 2002/0012059 to Wallerstein et al., which are incorporated herein by reference, describe a method for viewing an image. Light projected from the image is split into first and second bundles of light focusing over a first and a second focal region, respectively. The light at the first focal region is detected at a first resolution. The light at the second focal region is detected at a second resolution different from the first resolution.

U.S. Pat. No. 6,356,296 to Driscoll, Jr. et al., which is incorporated herein by reference, describes a panoptic camera system that can be used to capture all the light from a hemisphere viewing angle. The panoptic camera comprises a main reflecting mirror that reflects light from an entire hemisphere onto an image capture mechanism. The main reflecting mirror consists of a paraboloid shape with a dimple on an apex. The surface area around the dimple allows the main reflector to capture light from behind an image capture mechanism or a second reflector.

U.S. Pat. Nos. 6,459,451 and 6,424,377 to Driscoll, Jr. et al., which are incorporated herein by reference, describe a panoramic camera apparatus that captures a 360 degree panoramic image. The panoramic image is recorded as a two dimensional annular image. Techniques are described for digitally performing a geometric transformation of the two dimensional annular image into rectangular projections such that the panoramic image can be displayed using conventional methods.

U.S. Pat. No. 6,373,642 to Wallerstein et al., which is incorporated herein by reference, describes a panoramic imaging arrangement that includes a first lens block including a convex reflective surface and a transparent component. The convex reflective surface has a substantially vertically extending axis of revolution and is capable of receiving light from a 360 degree surrounding panoramic scene, and reflecting the light for further manipulation. The transparent component covers the convex reflective surface, so as to protect the convex reflective surface from environmental conditions.

U.S. Pat. No. 6,388,820 to Wallerstein et al., which is incorporated herein by reference, describes a panoramic imaging arrangement that includes at least a first lens block including a convex reflective surface and a transparent component. The convex reflective surface has a substantially vertically extending axis of revolution which is described as being capable of receiving light from a 360 degree surrounding panoramic scene, and reflecting the light for further manipulation. The transparent component covers the convex reflective surface. The convex reflective surface is thereby protected from environmental conditions which may otherwise result in damage to the convex reflective surface.

U.S. Pat. No. 6,597,520 to Wallerstein et al., which is incorporated herein by reference, describes a panoramic imaging arrangement comprising a first and second transparent component both rotationally symmetric about an axis of revolution. The first transparent component has an upper surface and a lower surface. The lower surface includes a reflective portion and a refractive portion both about the axis of revolution. The refractive portion extends radially from the axis of revolution to the start of the reflective portion. The second transparent component is attached to the first transparent component at a refractive interface that extends into the upper surface. The second transparent component includes a distal reflective surface. Light from a portion of a surrounding panoramic scene is refracted by a portion of the upper surface, and is reflected by the reflective portion of the lower surface through the refractive interface to the distal reflective surface. Once reflected from the distal reflective surface, the light again passes through the refractive interface and exits the first transparent component through the refractive portion of the lower surface.

U.S. Pat. No. 4,647,761 to Cojan et al., which is incorporated herein by reference, describes an airborne system for the electro-optical detection, location and omnidirectional tracking of a target. The system has an input objective lens carried by a universal joint, whereof one frame is rotated circularly in azimuth and the second frame moves the optic in elevation. An image offsetting optical section integral with the universal joint maintains the image centering through the detection plane, the detector being fixed. The image offsetting optical section is catadioptric and has an input mirror integral with the objective lens, and an output mirror integral with the first frame and which reflects the radiation along the circular rotation axis. The input objective lens focuses the radiation in an image plane located on the optical path between two mirrors, and a second optical objective lens re-forms the field image in the detection plane.

U.S. Pat. No. 5,790,182 to St. Hilaire, which is incorporated herein by reference, describes techniques for wide-angle imaging to create a high resolution image using a convex primary mirror concentrically positioned relative to a concave secondary mirror and one or more detectors spherically juxtaposed. The radii of the primary and secondary mirrors are related by the square of the "golden ratio" to reduce low order aberrations. A fiber optic faceplate coupled to each detector corrects field curvature of the image which may then be detected with a conventional flat detector.

U.S. Pat. No. 6,130,783 to Yagi et al., which is incorporated herein by reference, describes an omnidirectional panoramic visual sensor including a convex mirror with a surface of revolution having a focal point, a plurality of mirrors with surfaces of revolutions having at least one focal point, a photoreceiving lens system receiving light reflected by the convex mirror with the surface of revolution and the plurality of mirrors with surfaces of revolutions, and an image acquisition surface. The convex mirror and the plurality of mirrors are so arranged that the focal point of a first mirror included in the convex mirror and the plurality of mirrors aligns with the focal point of a second mirror, included in the convex mirror and the plurality of mirrors, further reflecting light reflected by the first mirror.

U.S. Pat. No. 6,646,818 to Doi, which is incorporated herein by reference, describes a panoramic imaging lens having an annular light incident surface formed in a substantial convex lens form; a first reflective surface formed in an annular concave mirror form to reflect light inside the lens; a second reflective surface provided at a central part inside the annular light incident surface to reflect the reflected light from the first reflective surface toward an inner part of the annular first reflective surface; and a light outgoing surface positioned at a central part inside the annular first reflective surface and opposing the second reflective surface to transmit light. A non-reflective part exerting no regular reflection of light is provided on a light path toward the light incident surface amongst light paths of light proceeding to agree with a light path of imaging light incident on and refracted at the light incident surface and proceeding inside the lens.

U.S. Pat. No. 6,222,683 to Hoogland et al., which is incorporated herein by reference, describes a panoramic imaging arrangement comprising a transparent component and a reflective material. The transparent component has a first surface about a vertical axis of revolution, a second surface about the axis of revolution, and an opening formed therein to define a third, internal surface about the axis of revolution. The third surface has a concave profile in a plane of the axis of revolution. The reflective material is located on the second surface to provide a reflective surface against the second surface. The first surface, the reflective surface, and the third surface are positioned relative to one another so that light from a 360 degree surrounding panoramic scene enters the transparent component through the first surface, is reflected from the reflective surface, and exits the transparent component through the third surface.

U.S. Pat. No. 6,304,285 to Geng, which is incorporated herein by reference, describes an omnidirectional imaging system comprising a reflective mirror for viewing object within a hemispherical field of view form a single virtual view point at the local center of said reflective mirror, a projector for projecting a light beam toward said reflective mirror, and a variable wavelength filter optically positioned between said projector and said reflective mirror for generating a pattern having a spatially distributed wavelength spectrum of said reflective mirror.

U.S. Pat. No. 5,473,474 to Powell, which is incorporated herein by reference, describes a panoramic imaging system for projecting a 360 degree cylindrical field of view onto a two-dimensional annular format. The system has a panoramic imaging block with a concentric axis of symmetry, two refractive surfaces and two reflective surfaces. The first reflective surface is a concave conicoid of revolution with the conic constant in the range of −0.6 to +2.0. In an embodiment of the invention, the second refractive surface (the last in the path of rays) is flat, while the first reflective surface, the second reflective surface, and the first refractive surface are all spherical.

U.S. Pat. No. 5,920,376 to Bruckstein et al., which is incorporated herein by reference, describes an omnidirectional or panoramic viewer/projector that uses a single camera and a mirror with a curved surface. The curved mirror provides a single virtual optical center or viewpoint.

U.S. Pat. No. 6,375,366 to Kato et al., which is incorporated herein by reference, describes an omnidirectional camera device that is able to restrict a range in which images of objects are detected. This omnidirectional camera device comprises a rotationally-symmetric convex mirror fixedly attached to one end of a transparent tube assembly, an image pickup means disposed on the other end of the tube assembly in an opposing relation to this convex mirror, and a cover assembly disposed on the tube assembly for restricting the range in which light becomes incident on the convex mirror. The cover assembly is mounted on one end side of the tube assembly, and is attached to the tube assembly so as to become freely rotatable.

U.S. Pat. No. 5,739,852 to Richardson et al., which is incorporated herein by reference, describes an electronic imaging system for capturing an image comprising a lens and an imaging sensor. The imaging sensor includes a plurality of imaging elements, the plurality of imaging elements having a distribution on the surface representable by a nonlinear function. The distribution of imaging elements has a relatively low density at a center point of the surface and a relatively high density at a point along a periphery of the surface.

U.S. Pat. No. 6,115,193 to Shu, which is incorporated herein by reference, describes a device for creating a panoramic field of view, comprising a first light-passing incident surface which is a cylinder surface and a second incident surface which is a mirror surface onto which light passing through the first surface impinges. A third incident surface onto which light from the second incident surface impinges is aspherical. A recollimating element for presenting a pupil plane depiction of a panoramic field of view is also provided.

U.S. Pat. No. 5,502,592 to Jamieson, which is incorporated herein by reference, describes a wide-aperture infrared lenses with hyper-hemispherical fields of view (e.g., up to 270 degree) and at wide relative apertures (e.g., up to f/0.7) to produce images having low distortion—typically no more than 20% greater than the distortion resulting when the image size is proportional to the field angle.

U.S. Pat. No. 4,012,126 to Rosendahl et al., which is incorporated herein by reference, describes an optical system for 360 degree image transfer in which spaced primary and secondary hyperbolically surfaced mirrors are combined with a refractive lens system and are held in spaced relation by a transparent envelope having inner and outer surfaces generated from the near focal point of the primary mirror to avoid ray pass through distortion, and in which the mirrors are so spaced and concentrically arranged that the entrance pupil of the lens system coincides with the near focal point of the primary mirror, which is centrally apertured to form an aperture stop (diaphragm), and the near focal point of the secondary mirror approximates the apex of the primary mirror, the far focal points of the mirrors coinciding to form a confocal set of mirrors.

U.S. Pat. No. 6,028,719 to Beckstead et al., which is incorporated herein by reference, describes an imaging system that comprises a panoramic imaging element. The panoramic imaging element is described as being capable of imaging a full 360 degree panoramic image and a forward image onto a single plane.

U.S. Pat. No. 6,704,148 to Kumata, which is incorporated herein by reference, describes an omnidirectional imaging device including a retainer having a top section, a body section, and a bottom section. A mirror having a surface of revolution is mounted on the top portion of the body section. The bottom section is assembled with a mounting base for movably mounting an image pickup device, and with a fixture for fixing the image pickup device to the mounting base.

U.S. Pat. No. 4,976,524 to Chiba, which is incorporated herein by reference, describes an optical system for endoscopes including at least one convex or concave aspheric surface, and a reflecting mirror arranged on the front side of the imaging optical system and having a reflecting surface shaped like a spherical or aspheric surface.

U.S. Pat. No. 6,611,282 to Trubko et al., which is incorporated herein by reference, describes a system for capturing super wide-angle panoramic images. In particular, a two-reflector system is described which is substantially self-correcting in which optical aberrations are substantially eliminated, such as field curvature, astigmatism and the like. In an embodiment of the invention, two reflectors (e.g., one a hyperboloidal mirror, the other a concave ellipsoidal or spherical mirror), a relay system (e.g., optics such as a mirror, a lens, or a pinhole), and an image sensor are provided.

U.S. Pat. No. 6,333,826 to Charles, which is incorporated herein by reference, describes an omniramic wide angle optical system comprising a Cassegrain system having a strongly curved convex reflecting surface with a prolate aspheric figure, a secondary reflector surface, and a modular imaging and correcting lens system. Also described is the conversion of a two dimensional annular image or a segment thereof to a viewable horizontal image or a subset thereof, or from a horizontal format image or a subset thereof into an annular image or a segment thereof.

U.S. Pat. No. 6,449,103 to Charles, which is incorporated herein by reference, describes an omnidirectional wide angle optical system comprising an external refracting surface which may be strongly curved, a strongly curved internal primary reflector surface, a secondary reflector surface, central wide angle refracting optics, a modular or integral imaging and correcting lens system which may have aperture adjustment means, and mounting components. Optical surfaces associated with the formation of an omidirectional virtual image are typically integrated into a single solid catadioptric optic in some embodiments, but central or peripheral wide angle refracting optics which may provide supplemental coverage are separate optical elements in other embodiments.

U.S. Pat. No. 6,157,018 to Ishiguro et al., which is incorporated herein by reference, describes an omnidirectional vision sensor that comprises a rotationally symmetrical convex mirror and a camera arranged opposite the mirror. The rays of light which internally reflect inside the cylinder pass through the production line of the rotational axis of the convex mirror, and are thus eliminated before they reach the inner surface of the transparent cylinder. A tapered object on the vertex of the convex mirror is described as completely eliminating inner reflected rays of light.

US Patent Application Publication 2002/0109773 to Kuriyama et al., which is incorporated herein by reference, describes an imaging device that includes a convex mirror for reflecting first incident light representing an object, the convex mirror having a shape of a solid of revolution; an imaging mechanism for capturing a reflected image represented by light reflected in the convex mirror; and an optical member for guiding the first incident light toward the convex mirror and guiding the reflected light toward the imaging mechanism. The optical member has an attenuation section for attenuating second incident light which (a) is incident on an outer circumferential surface of the optical member in a direction opposite the first incident light, (b) passes through the optical member, (c) is reflected by an inner circumferential surface of the optical member so as to be directed toward the convex rotational mirror, and (d) is superimposed on the first incident light.

US Patent Application Publication 2002/0109772 to Kuriyama et al., which is incorporated herein by reference, describes an imaging device including a convex mirror for reflecting incident light representing an object, the convex mirror having a shape of solid of revolution; an imaging mechanism for taking an image represented by reflected light from the convex mirror; and an optical member for guiding the incident light toward the convex mirror and guiding the reflected light toward the imaging mechanism, the optical member being in close contact with the convex mirror.

US Patent Application 2004/0004836 to Dubuc, which is incorporated herein by reference, describes an internal reflection element having a plurality of internal reflection faces and a plurality of exit faces which redirect light from a light source into a side direction. The curved entry faces have the optical effect of concentrating incident light onto a center of the corresponding internal reflection face. This is described as allowing light impinging on the internal reflection face from a wide range of angles to be redirected for side projection through the desired exit face.

US Patent Application Publication 2004/0249247 to Iddan, which is incorporated herein by reference, describes an endoscope capable of capturing images of an in-vivo area behind a distal end of the endoscope's tube. The endoscope has an imaging unit that includes a reflective surface that reflects an image of an area surrounding such tube onto an image sensor.

US Patent Application Publication 2003/0191369 to Arai et al., which is incorporated herein by reference, describes an omnidirectional endoscope device at a distal end part of an insertion section of an endoscope with an omnidirectional light receiving unit for receiving incident light from all around the periphery in the peripheral direction and reflecting the light toward a relay lens optical system. The insertion section slidably pierces a retaining cylinder. A light guide is embedded in the retaining cylinder, and an outgoing surface at the distal end of the light guide is faced with a distal end face of the retaining cylinder. The retaining cylinder can be operated in a sliding manner by a grip disposed at the basal end. The light thereby strikes the view field of the omnidirectional light receiving mechanism regardless of whether the inside space of an image to be observed is large or small.

PCT Publication WO 01/68540 to Friend, which is incorporated herein by reference, describes an imaging apparatus comprising two imaging units for producing images of respective scenes, each imaging unit comprising optical means for gathering light over a wide sector and directing it to image sensing means. The optical means of the imaging units can be back-to-back so as to encompass the imaging sensing means and each unit can include a convex reflector for reflecting light from a panoramic scene onto a planar reflector which reflects light through a port or ports in the convex reflector onto a CCD array within the convex reflector.

PCT Publication WO 02/059676 to Gal et al., which is incorporated herein by reference, describes a spherical view imaging apparatus comprising an axisymmetric form comprising a transparent lateral surface, a first end surface, and a second end surface; a first lens positioned substantially perpendicular to and concentric with the axis of the axisymmetric form to the side of the first end surface; a second lens positioned substantially perpendicular to and concentric with the axis of the axisymmetric form on the side of the second end surface; and an image acquiring device positioned substantially coaxially with the second lens and beyond the second lens with respect to the second end surface.

PCT Publication WO 03/026272 to Gal et al., which is incorporated herein by reference, describes an imaging assembly comprising a first, essentially symmetric reflective surface, having a shape suitable to reflect a substantially panoramic view of an area surrounding it, and a second reflective surface, which is asymmetric with respect to said first reflective surface, i.e., which is positioned, with respect to the axis of symmetry of said first reflective surface, such that its movement in one or more directions reflects different portions of the area reflected by said first reflective surface, and the optical properties of said second reflective surface are such that area imaged by it is magnified with respect to the same portion of the area imaged by the first reflective surface.

PCT Publication WO 02/075348 to Gal et al., which is incorporated herein by reference, describes a method for determining azimuth and elevation angles of a radiation source or other physical objects located anywhere within an cylindrical field of view. The method uses an omni-directional imaging system including reflective surfaces, an image sensor, and an optional optical filter for filtration of the desired wavelengths. Use of two such systems separated by a known distance, each providing a different reading of azimuth and elevation angle of the same object, enables classic triangulation for determination of the actual location of the object.

PCT Publication WO 03/046830 to Gal et al., which is incorporated herein by reference, describes a self-contained omnidirectional imaging device. The device contains within it all mechanic, electronic, optic and electro-optic components required for its operation, namely: omnidirectional optics, image capture device, power source, illumination sources, transmitters, receivers, and additional optional elements for enhanced capabilities. In an embodiment, the device is housed inside a spherical structure, designed for deployment to potentially hazardous environments, in order to enable omnidirectional viewing of such environments without endangering the viewer.

PCT Publication WO 04/042428 to Gal et al., which is incorporated herein by reference, describes an omni-directional imaging assembly, which comprises a solid omni-directional lens comprising a vertical axis of symmetry; an upper surface, at least part of which is capable of reflecting rays that arrive from the inner side of the omni-directional lens; a transparent perimeter surface; a lower convex surface, at least part of which is capable of reflecting rays that arrive from the direction of the perimeter surface; and a transparent circular surface maintained in the lower convex surface around the vertical axis of symmetry. The light rays from a first 360 degree, panoramic, scene are refracted by the transparent perimeter surface, are then reflected by the lower convex surface towards the upper surface, and are then reflected by the upper surface towards the transparent circular surface, where they are refracted and exit the omni-directional lens. For some applications, the imaging assembly is combined with an illumination source to simultaneously provide both omni-directional imaging and omni-directional illumination. Also described are embodiments that comprise image capturing devices, embodiments that enable simultaneous imaging of the first scene and a second scene, and embodiments that are adapted to the requirements of endoscopic imaging.

PCT Publication WO 03/096078 to Gal, which is incorporated herein by reference, describes electro-optical assemblies, which are capable of capturing a full or nearly full spherical field of view.

PCT Publication WO 03/054625 to Gal et al., which is incorporated herein by reference, describes apparatus for panoramic stereoscopic imaging, comprising a first panoramic imaging assembly located at a first location, and a second panoramic imaging assembly located at a second location. The locations are located on a platform, which is a common horizontal plane.

PCT Publication WO 04/008185 to Gal et al., which is incorporated herein by reference, describes a wide-angle imaging assembly which comprises a main lens produced from an aspheric optical block. The aspheric optical block comprises a vertical axis of symmetry; a transparent upper surface, at least part of which is capable of reflecting rays that impinge upon it from the interior of the optical block; a transparent perimeter surface; and a transparent lower surface. The optical block is fabricated from material selected to enable optical transmittance of a specific spectral range. Light rays in the specific spectral range originating in a first scene, having a 360 degree panoramic perimeter, are refracted by the transparent perimeter surface, enter the optical block, are then reflected by the upper surface towards the transparent lower surface, where they are then refracted by the transparent lower surface, and exit through it.

Japanese Patent Application Publication JP 61-267725 A2 to Miyazaki Atsushi, which is incorporated herein by reference, describes an endoscope fitted with a conical surface-like mirror for observing both the side and the front of a pipe.

Japanese Patent Application Publication JP 71-91269 A2 to Yamamoto Katsuro et al., which is incorporated herein by reference, describes an endoscope having an irradiation port at a tip of a light guide. The port directly illuminates an observed surface, and the image of the observed surface is projected and reflected on a conical mirror.

SUMMARY OF THE INVENTION

In embodiments of the present invention, an optical system for use with a device comprises an optical assembly and an image sensor, such as a CCD or CMOS sensor. Typically, the device comprises an endoscope for insertion in a lumen. For some applications, the endoscope comprises a colonoscope, and the lumen includes a colon of a patient. The optical assembly typically comprises an optical member having a rotational shape, at least a distal portion of which is shaped so as to define a curved lateral surface. A distal (forward) end of the optical assembly comprises a convex mirror having a rotational shape that has the same rotation axis as the optical member. (The mirror is labeled "convex" because, as described hereinbelow with reference to the figures, a convex surface of the mirror reflects light striking the mirror, thereby directing the light towards the image sensor.)

The optical system is configured to enable simultaneous forward and omnidirectional lateral viewing. Light arriving from the forward end of the optical member, and light arriving from the lateral surface of the optical member travel through substantially separate, non-overlapping optical paths. The forward light and the lateral light are typically processed to create two separate images, rather than a unified image. The optical assembly is typically configured to provide different levels of magnification for the forward light and the lateral light. For some applications, the forward view is used primarily for navigation within a body region, while the omnidirectional lateral view is used primarily for inspection of the body region. In these applications, the optically assembly is typically configured such that the magnification of the forward light is less than that of the lateral light.

The optical member is typically shaped so as to define a distal indentation at the distal end of the optical member, i.e., through a central portion of the mirror. A proximal surface of the distal indentation is shaped so as to define a lens that focuses light passing therethrough. In addition, for some applications, the optical member is shaped so as to define a proximal indentation at the proximal end of the optical member. At least a portion of the proximal indentation is shaped so as to define a lens. It is noted that for some applications, the optical member is shaped so as to define a distal protrusion, instead of a distal indentation. Alternatively, the optical member is shaped so as to define a surface (refracting or non-refracting) that is generally flush with the mirror, and which allows light to pass therethrough.

In some embodiments of the present invention, the optical assembly further comprises a distal lens that has the same rotation axis as the optical member. The distal lens focuses light arriving from the forward direction onto the proximal surface of the distal indentation. For some applications, the optical assembly further comprises one or more proximal lenses, e.g., two proximal lenses. The proximal lenses are positioned between the optical member and the image sensor, so as to focus light from the optical member onto the image sensor.

In some embodiments of the present invention, the optical system comprises a light source, which comprises two concentric rings of LEDs encircling the optical member: a side-lighting LED ring and a forward-lighting LED ring. The LEDs of the side-lighting LED ring are oriented such that they illuminate laterally, in order to provide illumination for omnidirectional lateral viewing by the optical system. The LEDs of the forward-lighting LED ring are oriented such that they illuminate in a forward direction, by directing light through the optical member and the distal lens. For some applications, the light source further comprises one or more beam shapers and/or diffusers to narrow or broaden, respectively, the light beams emitted by the LEDs.

Alternatively, the light source comprises a side-lighting LED ring encircling the optical member, and a forward-lighting LED ring positioned in a vicinity of a distal end of the optical member. The LEDs of the forward-lighting LED ring are oriented such that they illuminate in a forward direction. The light source typically provides power to the forward LEDs over at least one power cable, which typically passes along the side of the optical member. For some applications, the power cable is oriented diagonally with respect to a rotation axis of the optical member. Because of movement of the optical system through the lumen, such a diagonal orientation minimizes or eliminates visual interference that otherwise may be caused by the power cable.

In some embodiments of the present invention, the optical system is configured to alternatingly activate the side-lighting and forward-lighting light sources. Image processing circuitry of the endoscope is configured to process forward viewing images only when the forward-viewing light source is illuminated and the side-viewing light source is not illuminated, and to process lateral images only when the side-lighting light source is illuminated and the forward-viewing light source is not illuminated. Such toggling typically reduces any interference that may be caused by reflections caused by the other light source, and/or reduces power consumption and heat generation.

In some embodiments of the present invention, image processing circuitry is configured to capture a series of longitudinally-arranged image segments of an internal wall of a lumen in a subject, while the optical system is moving through the lumen (i.e., being either withdrawn or inserted). The image processing circuitry stitches together individual image segments into a combined continuous image. This image capture and processing technique generally enables higher-magnification imaging than is possible using conventional techniques, ceteris paribus. Using conventional techniques, a relatively wide area must generally be captured simultaneously in order to provide a useful image to the physician. In contrast, the techniques described herein enable the display of such a wide area while only capturing relatively narrow image segments. This enables the optics of the optical system to be focused narrowly on an area of wall having a width approximately equal to that of each image segment.

In some embodiments of the present invention, image processing circuitry produces a stereoscopic image by capturing two images of each point of interest from two respective viewpoints while the optical system is moving, e.g., through a lumen in a subject. For each set of two images, the location of the optical system is determined. Using this location information, the image processing software processes the two images in order to generate a stereoscopic image.

In some embodiments of the present invention, image processing circuitry converts a lateral omnidirectional image of a lumen in a subject to a two-dimensional image. Typically, the image processing circuitry longitudinally cuts the omnidirectional image, and then unrolls the omnidirectional image onto a single plane.

There is therefore provided, in accordance with an embodiment of the present invention, apparatus including an optical system for use in an endoscope, the optical system having distal and proximal ends and including:

an image sensor, positioned at the proximal end of the optical system;

an optical member having distal and proximal ends, and shaped so as to define:

a lateral surface, at least a distal portion of which is curved, configured to provide omnidirectional lateral viewing, a distal indentation in the distal end of the optical member, and a proximal indentation in the proximal end of the optical member;

a convex mirror, coupled to the distal end of the optical member, and shaped so as define an opening through which the distal indentation passes; and a distal lens, positioned distal to the mirror, wherein the optical member, the mirror, and the distal lens have respective rotational shapes about a common rotation axis.

In an embodiment, the optical member and the distal lens are configured to provide different levels of magnification for distal light arriving at the image sensor through the distal end of the optical system, and lateral light arriving at the image sensor through the curved distal portion of the lateral surface of the optical member.

In an embodiment, the distal lens is shaped so as to define a distal convex aspheric surface and a proximal concave aspheric surface.

In an embodiment, the optical system includes one or more proximal lenses, positioned between the optical member and the image sensor.

In an embodiment, a proximal surface of the distal indentation is shaped so as to define a lens.

In an embodiment, at least a portion of the proximal indentation is shaped so as to define a lens.

There is further provided, in accordance with an embodiment of the present invention, apparatus including an optical system for use in an endoscope, the optical system having distal and proximal ends and including:
 an image sensor, positioned at the proximal end of the optical system;
 an optical member having distal and proximal ends, and shaped so as to define:
  a lateral surface, at least a distal portion of which is curved, configured to provide omnidirectional lateral viewing, and
  a distal indentation in the distal end of the optical member, the indentation shaped so as to define a lens at a proximal surface thereof; and
 a convex mirror, coupled to the distal end of the optical member, and shaped so as define an opening through which the rotation distal indentation passes, wherein the optical member and the mirror have respective rotational shapes about a common rotation axis.

There is yet further provided, in accordance with an embodiment of the present invention, apparatus including an optical system for use in an endoscope, the optical system having distal and proximal ends and including:
 an image sensor, positioned at the proximal end of the optical system;
 an optical member having distal and proximal ends, and shaped so as to define a lateral surface, at least a distal portion of which is curved, configured to provide omnidirectional lateral viewing;
 a convex mirror, coupled to the distal end of the optical member, and shaped so as define an opening through which distal light passes, wherein the optical member and the mirror have respective rotational shapes about a common rotation axis;
 a light source; and
 a power cable, coupled to the light source, and positioned diagonally with respect to the common rotation axis, along a portion of the curved distal portion of the lateral surface of the optical member.

In an embodiment, the optical system includes image processing circuitry, configured to replace an image of an area of interest captured at a first point in time at which the area is blocked by the power cable, with an image of the area captured at a second point in time at which the area is not blocked by the power cable.

There is still further provided, in accordance with an embodiment of the present invention, apparatus including an optical system for use in an endoscope, the optical system having distal and proximal ends and including:
 an image sensor, positioned at the proximal end of the optical system;
 an optical member having distal and proximal ends, and shaped so as to define a lateral surface, at least a distal portion of which is curved, configured to provide omnidirectional lateral viewing;
 a convex mirror, coupled to the distal end of the optical member, and shaped so as define an opening through which distal light passes to provide forward viewing, wherein the optical member and the mirror have respective rotational shapes about a common rotation axis;
 a side-lighting light source, adapted to provide lighting lateral to the optical member;
 a forward-lighting light source, adapted to provide lighting distal to the optical member;
 a control unit, adapted to alternatingly activate the side-lighting and forward-lighting light sources; and
  image processing circuitry, configured to:
  process a forward viewing image sensed by the image sensor during a time of activation of the forward-lighting light source and inactivation of the side-lighting light source, and
  process an omnidirectional lateral viewing image sensed by the image sensor during a time of activation of the side-lighting light source and inactivation of the forward-lighting light source.

There is also provided, in accordance with an embodiment of the present invention, apparatus including an optical system for use in an endoscope, the optical system including:
 an image sensor;
 an optical member, configured to provide lateral viewing of a body lumen in which the endoscope is inserted; and
  image processing circuitry, configured to:
  capture from the image sensor a series of longitudinally-arranged image segments of an internal wall of the lumen, while the optical member is moving through the lumen, and
  stitch together the series of image segments into a combined continuous image.

In an embodiment, the optical member is configured to provide omnidirectional lateral viewing of the lumen.

In an embodiment, the image processing circuitry is configured to:
 capture the series of image segments such that adjoining image segments share respective overlapping portions of an image of the lumen wall, and
 align the series of image segments by using information from the overlapping portions to register successive image segments with one another.

There is additionally provided, in accordance with an embodiment of the present invention, a method including:
 moving an optical member through a body lumen;
 capturing, via the optical member, a series of longitudinally-arranged image segments of an internal wall of the lumen, while the optical member is moving through the lumen; and
 stitching together the series of image segments into a combined continuous image.

In an embodiment, the image segments include omnidirectional image segments, and wherein capturing includes capturing the series of omnidirectional longitudinally-arranged image segments.

In an embodiment, capturing includes capturing the series of image segments such that adjoining image segments share respective overlapping portions of an image of the lumen wall, and wherein stitching includes aligning the series of image segments by using information from the overlapping portions to register successive image segments with one another.

There is yet additionally provided, in accordance with an embodiment of the present invention, apparatus including an optical system for use in an endoscope, the optical system having distal and proximal ends and including:

an image sensor, positioned at the proximal end of the optical system;

an optical member having distal and proximal ends, and shaped so as to define:

a lateral surface, at least a distal portion of which is curved, configured to provide omnidirectional lateral viewing, a distal indentation in the distal end of the optical member, and a proximal indentation in the proximal end of the optical member;

a convex mirror, coupled to the distal end of the optical member, and shaped so as define an opening through which the distal indentation passes; and a distal lens, positioned distal to the mirror, wherein the optical member, the mirror, and the distal lens have respective rotational shapes about a common rotation axis, and wherein the optical member and the distal lens are configured to provide different levels of magnification for distal light arriving at the image sensor through the distal end of the optical system, and lateral light arriving at the image sensor through the curved distal portion of the lateral surface of the optical member.

There is also provided, in accordance with an embodiment of the present invention, apparatus including an optical system for use in an endoscope, the optical system having distal and proximal ends and including:

an image sensor, positioned at the proximal end of the optical system;

an optical member having distal and proximal ends, and shaped so as to define:

a lateral surface, at least a distal portion of which is curved, configured to provide omnidirectional lateral viewing, and a distal indentation in the distal end of the optical member, the indentation shaped so as to define a lens at a proximal surface thereof; and a convex mirror, coupled to the distal end of the optical member, and shaped so as define an opening through which the rotation distal indentation passes, wherein the optical member and the mirror have respective rotational shapes about a common rotation axis.

There is further provided, in accordance with an embodiment of the present invention, apparatus including an optical system for use in an endoscope, the optical system having distal and proximal ends and including:

an image sensor, positioned at the proximal end of the optical system;

an optical member having distal and proximal ends, and shaped so as to define a lateral surface, at least a distal portion of which is curved, configured to provide omnidirectional lateral viewing;

a convex mirror, coupled to the distal end of the optical member, and shaped so as define an opening through which distal light passes, wherein the optical member and the mirror have respective rotational shapes about a common rotation axis;

a light source; and a power cable, coupled to the light source, and positioned diagonally with respect to the common rotation axis, along a portion of the curved distal portion of the lateral surface of the optical member.

There is still further provided, in accordance with an embodiment of the present invention, apparatus including an optical system for use in an endoscope, the optical system having distal and proximal ends and including:

an image sensor, positioned at the proximal end of the optical system;

an optical member having distal and proximal ends, and shaped so as to define a lateral surface, at least a distal portion of which is curved, configured to provide omnidirectional lateral viewing;

a convex mirror, coupled to the distal end of the optical member, and shaped so as define an opening through which distal light passes to provide forward viewing, wherein the optical member and the mirror have respective rotational shapes about a common rotation axis;

a side-lighting light source, adapted to provide lighting lateral to the optical member;

a forward-lighting light source, adapted to provide lighting distal to the optical member;

a control unit, adapted to alternatingly activate the side-lighting and forward-lighting light sources; and image processing circuitry, configured to:

process a forward viewing image sensed by the image sensor during a time of activation of the forward-lighting light source and inactivation of the side-lighting light source, and process an omnidirectional lateral viewing image sensed by the image sensor during a time of activation of the side-lighting light source and inactivation of the forward-lighting light source.

The present invention will be more fully understood from the following detailed description of preferred embodiments thereof, taken together with the drawings, in which:

DETAILED DESCRIPTION OF EMBODIMENTS

Figure 1:
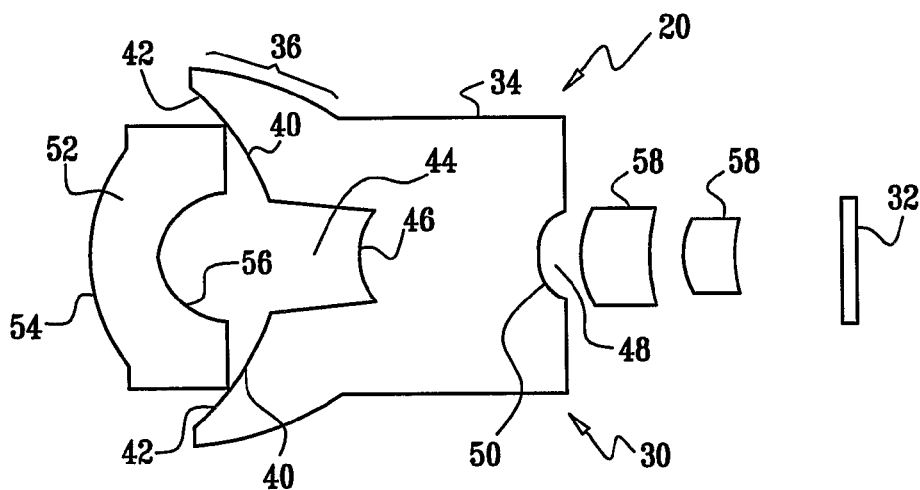
FIG. 1 is a schematic cross-sectional illustration of an optical system for use in an endoscope, in accordance with an embodiment of the present invention.

FIG. 1 is a schematic cross-sectional illustration of an optical system 20 for use in an endoscope (e.g., a colonoscope), in accordance with an embodiment of the present invention. Optical system 20 comprises an optical assembly 30 and an image sensor 32, such as a CCD or CMOS sensor. Optical system 20 further comprises mechanical support structures, which, for clarity of illustration, are not shown in the figure. Optical system 20 is typically integrated into the distal end of an endoscope (integration not shown).

Optical assembly 30 comprises an optical member 34 having a rotational shape. Typically, at least a distal portion 36 of the optical member is shaped so as to define a curved lateral surface, e.g., a hyperbolic, parabolic, ellipsoidal, conical, or semi-spherical surface. Optical member 34 comprises a transparent material, such as acrylic resin, polycarbonate, or glass. For some applications, all or a portion of the lateral surface of optical member 34 other than portion 36 is generally opaque, in order to prevent unwanted light from entering the optical member.

Optical assembly 30 further comprises, at a distal end thereof, a convex mirror 40 having a rotational shape that has the same rotation axis as optical member 34. Mirror 40 is typically aspheric, e.g., hyperbolic or conical. Alternatively, mirror 40 is semi-spherical. Mirror 40 is typically formed by coating a forward-facing concave portion 42 of optical member 34 with a non-transparent reflective coating, e.g., aluminum, silver, platinum, a nickel-chromium alloy, or gold. Such coating may be performed, for example, using vapor deposition, sputtering, or plating. Alternatively, mirror 40 is formed as a separate element having the same shape as concave portion 42, and the mirror is subsequently coupled to optical member 34.

Optical member 34 is typically shaped so as to define a distal indentation 44 at the distal end of the optical member, i.e., through a central portion of mirror 40. Distal indentation 44 typically has the same rotation axis as optical member 34. A proximal surface 46 of distal indentation 44 is shaped so as to define a lens that focuses light passing therethrough. Alternatively, proximal surface 46 is non-focusing. For some applications, optical member 34 is shaped so as to define a distally-facing protrusion from mirror 40. Alternatively, optical member 34 is shaped without indentation 44, but instead mirror 40 includes a non-mirrored portion in the center thereof.

For some applications, optical member 34 is shaped so as to define a proximal indentation 48 at the proximal end of the optical member. Proximal indentation 48 typically has the same rotation axis as optical member 34. At least a portion of proximal indentation 48 is shaped so as to define a lens 50. For some applications, lens 50 is aspheric.

In an embodiment of the present invention, optical assembly 30 further comprises a distal lens 52 that has the same rotation axis as optical member 34. Distal lens 52 focuses light arriving from the forward (proximal) direction onto proximal surface 46 of distal indentation 44, as described hereinbelow with reference to FIG. 2A. For some applications, distal lens 52 is shaped so as to define a distal convex aspheric surface 54, and a proximal concave aspheric surface 56. Typically, the radius of curvature of proximal surface 56 is less than that of distal surface 54. Distal lens 52 typically comprises a transparent optical plastic material such as acrylic resin or polycarbonate, or it may comprise glass.

For some applications, optical assembly 30 further comprises one or more proximal lenses 58, e.g., two proximal lenses 58. Proximal lenses 58 are positioned between optical member 34 and image sensor 32, so as to focus light from the optical member onto the image sensor. Typically, lenses 58 are aspheric, and comprise a transparent optical plastic material, such as acrylic resin or polycarbonate, or they may comprise glass.

Figure 2A:
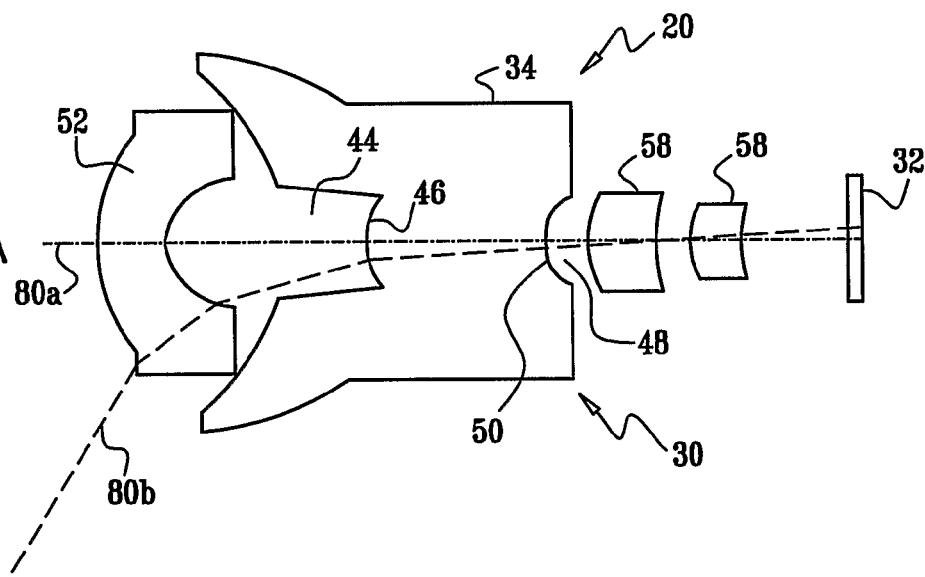
FIGS. 2A and 2B are schematic cross-sectional illustrations of light passing through the optical system of FIG. 1, in accordance with an embodiment of the present invention.
Figure 2B:
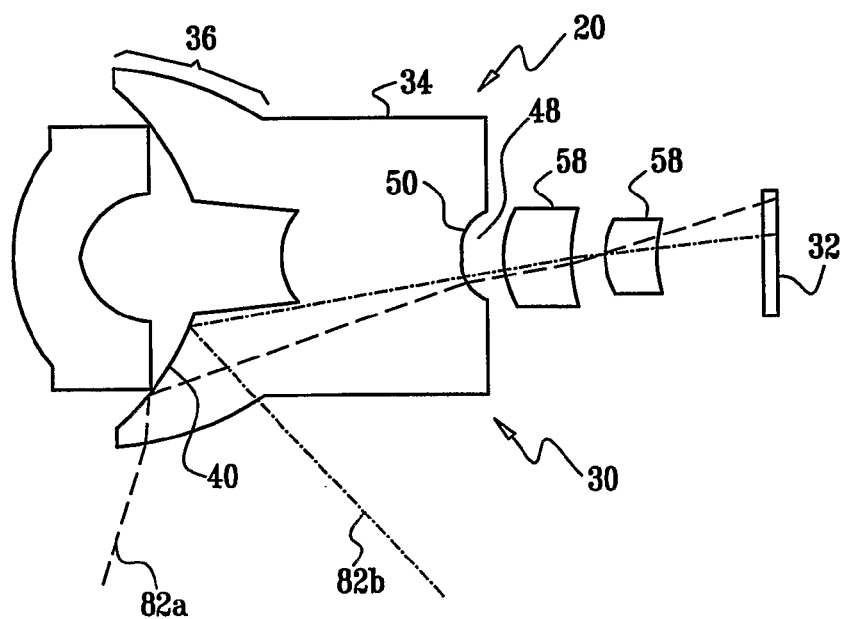

Reference is now made to FIGS. 2A and 2B, which are schematic cross-sectional illustrations of light passing through optical system 20, in accordance with an embodiment of the present invention. Optical system 20 is configured to enable simultaneous forward and omnidirectional lateral viewing. As shown in FIG. 2A, forward light, symbolically represented as lines 80a and 80b, enters optical assembly 30 distal to the assembly. Typically, the light passes through distal lens 52, which focuses the light onto proximal surface 46 of distal indentation 44. Proximal surface 46 in turn focuses the light onto lens 50 of proximal indentation 48, which typically further focuses the light onto proximal lenses 58. The proximal lenses still further focus the light onto image sensor 32, typically onto a central portion of the image sensor.

As shown in FIG. 2B, lateral light, symbolically represented as lines 82a and 82b, laterally enters optical assembly 30. The light is refracted by distal portion 36 of optical member 34, and then reflected by mirror 40. The light then passes through lens 50 of proximal indentation 48, which typically further focuses the light onto proximal lenses 58. The proximal lenses still further focus the light onto image sensor 32, typically onto a peripheral portion of the image sensor.

As can be seen, the forward light and the lateral light travel through substantially separate, non-overlapping optical paths. The forward light and the lateral light are typically processed to create two separate images, rather than a unified image. Optical assembly 30 is typically configured to provide different levels of magnification for the forward light and the lateral light. The magnification of the forward light is typically determined by configuring the shape of distal lens 52, proximal surface 46, and the central region of lens 50 of proximal indentation 48. On the other hand, the magnification of the lateral light is typically determined by configuring the shape of distal portion 36 of optical member 34 and the peripheral region of lens 50 of proximal indentation 48.

For some applications, the forward view is used primarily for navigation within a body region, while the omnidirectional lateral view is used primarily for inspection of the body region. In these applications, optically assembly 30 is typically configured such that the magnification of the forward light is less than that of the lateral light.

Figure 3:
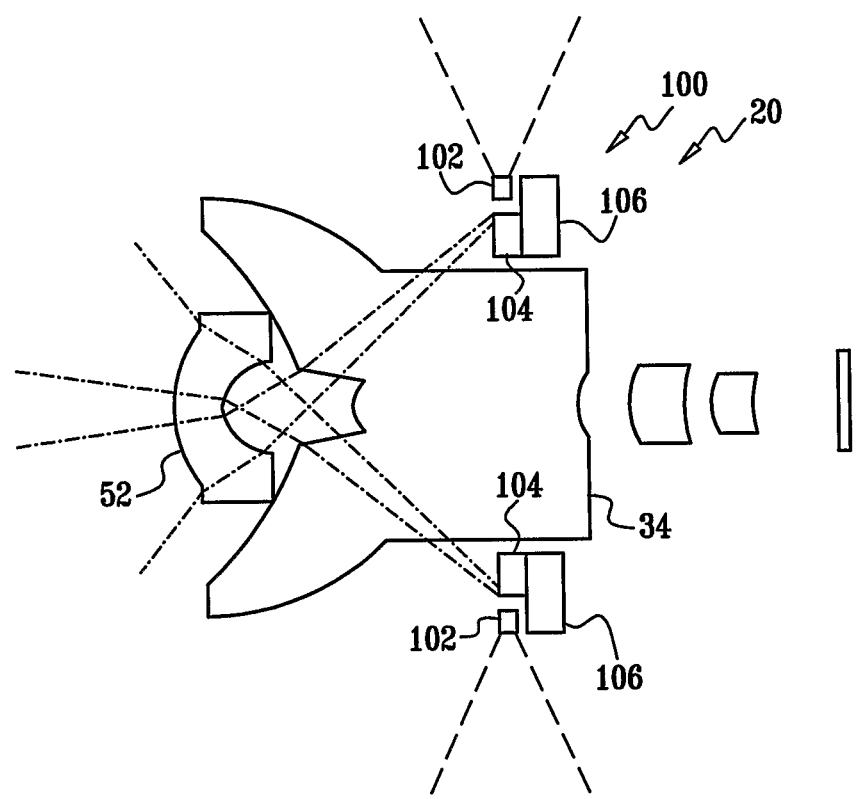
FIG. 3 is a schematic cross-sectional illustration of a light source for use in an endoscope, in accordance with an embodiment of the present invention.

Reference is now made to FIG. 3, which is a schematic cross-sectional illustration of a light source 100 for use in an endoscope, in accordance with an embodiment of the present invention. Although light source 100 is shown and described herein as being used with optical system 20, the light source may also be used with other endoscopic optical systems that provide both forward and lateral viewing.

Light source 100 comprises two concentric rings of LEDs encircling optical member 34: a side-lighting LED ring 102 and a forward-lighting LED ring 104. Each of the rings typically comprises between about 4 and about 12 individual LEDs. The LEDs are typically supported by a common annular support structure 106. Alternatively, the LEDs of each ring are supported by separate support structures, or are supported by optical member 34 (configurations not shown). Alternatively or additionally, light source 100 comprises one or more LEDs (or other lights) located at a different site, but coupled to support structure 106 via optical fibers (configuration not shown). It is thus to be appreciated that embodiments described herein with respect to LEDs directly illuminating an area could be modified, mutatis mutandis, such that light is generated at a remote site and conveyed by optical fibers. As appropriate for various applications, suitable remote sites may include a site near the image sensor, a site along the length of the endoscope, or a site external to the lumen.

The LEDs of side-lighting LED ring 102 are oriented such that they illuminate laterally, in order to provide illumination for omnidirectional lateral viewing by optical system 20. The LEDs of forward-lighting LED ring 104 are oriented such that they illuminate in a forward direction, by directing light through optical member 34 and distal lens 52. Typically, as shown in FIG. 3, side-lighting LED ring 102 is positioned further from optical member 34 than is forward-lighting LED ring 104. Alternatively, the side-lighting LED ring is positioned closer to optical member 34 than is the forward-lighting LED ring. For example, the LEDs of the rings may be positioned such that the LEDs of the forward-lighting LED ring do not block light emitted from the LEDs of the side-lighting LED ring, or the side-lighting LED ring may be placed distal or proximal to the forward-lighting LED ring (configurations not shown).

For some applications, light source 100 further comprises one or more beam shapers and/or diffusers to narrow or broaden, respectively, the light beams emitted by the LEDs. For example, beam shapers may be provided to narrow the light beams emitted by the LEDs of forward-lighting LED ring 104, and/or diffusers may be provided to broaden the light beams emitted by the LEDs of side-lighting LED ring 102.

Figure 4:
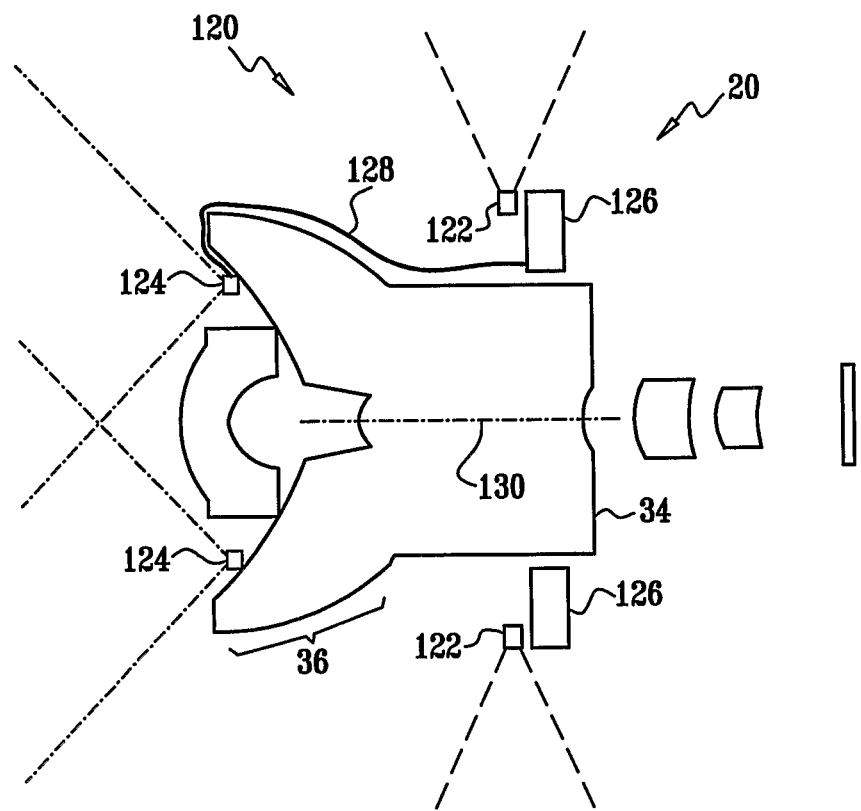
FIG. 4 is a schematic cross-sectional illustration of another light source for use in an endoscope, in accordance with an embodiment of the present invention.

Reference is now made to FIG. 4, which is a schematic cross-sectional illustration of a light source 120 for use in an endoscope, in accordance with an embodiment of the present invention. Although light source 120 is shown and described as being used with optical system 20, the light source may also be used with other endoscopic optical systems that provide both forward and lateral viewing.

Light source 120 comprises a side-lighting LED ring 122 encircling optical member 34, and a forward-lighting LED ring 124 positioned in a vicinity of a distal end of optical member 34. Each of the rings typically comprises between about 4 and about 12 individual LEDs. The LEDs of side-lighting LED ring 122 are oriented such that they illuminate laterally, in order to provide illumination for omnidirectional lateral viewing by optical system 20. The LEDs of side-lighting LED ring 122 are typically supported by an annular support structure 126, or by optical member 34 (configuration not shown).

The LEDs of forward-lighting LED ring 124 are oriented such that they illuminate in a forward direction. The LEDs of forward-lighting LED ring 124 are typically supported by optical member 34. Light source 120 typically provides power to the LEDs over at least one power cable 128, which typically passes along the side of optical member 34. (For some applications, power cable 128 is flush with the side of optical member 34.) In an embodiment, power cable 128 is oriented diagonally with respect to a rotation axis 130 of optical member 34, as the cable passes distal portion 36. (In other words, if power cable 128 passes the proximal end of distal portion 36 at "12 o'clock," then it may pass the distal end of distal portion 36 at "2 o'clock.") As described hereinbelow, such a diagonal orientation minimizes or eliminates visual interference that otherwise may be caused by the power cable.

For some applications, light source 120 further comprises one or more beam shapers and/or diffusers to narrow or broaden, respectively, the light beams generated by the LEDs. For example, diffusers may be provided to broaden the light beams generated by the LEDs of side-lighting LED ring 122 and/or forward-lighting LED ring 124.

Although light source 100 (FIG. 3) and light source 120 (FIG. 4) are described herein as comprising LEDs, the light sources may alternatively or additionally comprise other illuminating elements. For example, the light sources may comprise optical fibers illuminated by a remote light source, e.g., external to the endoscope or in the handle of the endoscope.

In an embodiment of the present invention, optical system 20 comprises a side-lighting light source and a forward-lighting light source. For example, the side-lighting light source may comprise side-lighting LED ring 102 or side-lighting LED ring 122, or any other side-lighting light source known in the art. Similarly, the forward-lighting light source may comprise forward-lighting LED ring 104 or forward-lighting LED ring 124, or any other forward-lighting light source known in the art. Optical system 20 is configured to alternatingly activate the side-lighting and forward-lighting light sources, typically at between about 10 and about 20 Hz, although faster or slower rates may be appropriate depending on the desired temporal resolution of the imaging data.

For some applications, only one of the light sources is activated for a desired length of time (e.g., greater than one minute), and video data are displayed based on the images illuminated by that light source. For example, the forward-lighting light source may be activated during initial advancement of a colonoscope to a site slightly beyond a target site of interest, and the side-lighting light source may be activated during slow retraction of the colonoscope, in order to facilitate close examination of the target site.

Image processing circuitry of the endoscope is configured to process forward-viewing images that were sensed by image sensor 32 during activation of the forward-viewing light source, when the side-viewing light source was not activated. The image processing circuitry is configured to process lateral images that were sensed by image sensor 32 during activation of the side-lighting light source, when the forward-viewing light source was not activated. Such toggling reduces any interference that may be caused by reflections caused by the other light source, and/or reduces power consumption and heat generation. For some applications, such toggling enables optical system 20 to be configured to utilize at least a portion of image sensor 32 for both forward and side viewing.

In an embodiment, a duty cycle is provided to regulate the toggling. For example, the lateral images may be sampled for a greater amount of time than the forward-viewing images (e.g., at time ratios of 1.5:1, or 3:1). Alternatively, the lateral images may be sampled for a lesser amount of time than the forward-viewing images.

In an embodiment, in order to reduce a possible sensation of image flickering due to the toggling, each successive lateral image is continuously displayed until the next lateral image is displayed, and, correspondingly, each successive forward-viewing image is continuously displayed until the next forward-viewing image is displayed. (The lateral and forward-viewing images are displayed on different portions of a monitor.) Thus, for example, even though the sampled forward-viewing image data may include a large amount of dark video frames (because forward illumination is alternated with lateral illumination), substantially no dark frames are displayed.

Figure 5:
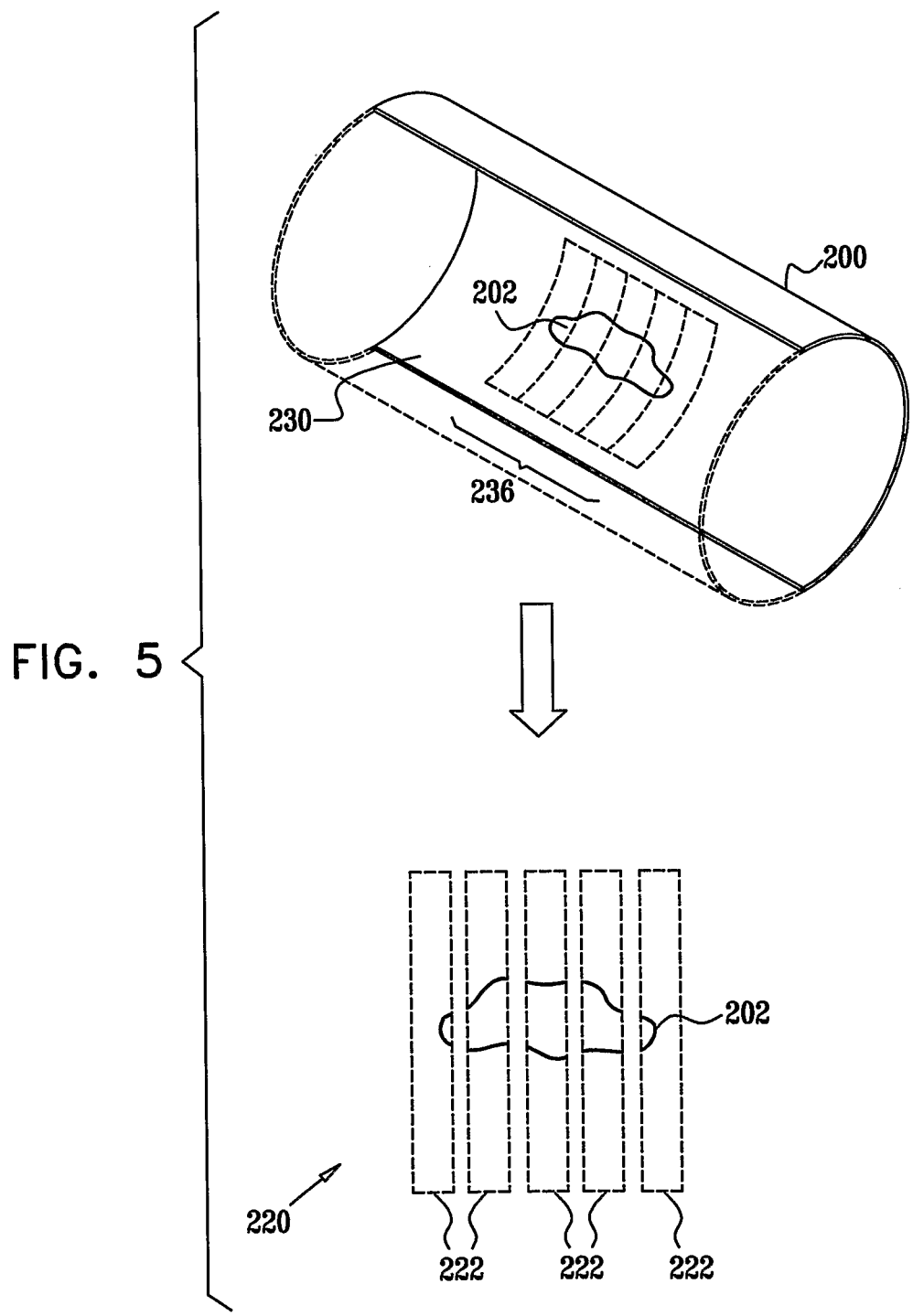
FIG. 5 is a schematic illustration of a lumen within a subject, in accordance with an embodiment of the present invention.

Reference is now made to FIG. 5, which is a schematic illustration of a lumen 200 within a subject, such as a gastrointestinal (GI) tract, in accordance with an embodiment of the present invention. An item of interest 202, such as a suspected tumor, is being examined. An endoscopic system comprises an optical system and image processing circuitry. The optical system is typically, but not necessarily, configured to enable omnidirectional lateral viewing (e.g., as described hereinabove).

The image processing circuitry is configured to capture a series 220 of longitudinally-arranged image segments 222 of an internal wall 230 of lumen 200, while the optical system is moving through the lumen (i.e., being either withdrawn or inserted). The image processing circuitry stitches together individual image segments 222 into a combined continuous image, either in real time and/or for later viewing. The image processing circuitry typically accurately aligns image segments 222 for such stitching using one or both of the following techniques:

Image segments 222 are captured such that adjoining segments share an overlapping portion of the image. The image processing circuitry uses information from this overlapping portion to register successive segments.

The endoscopic system detects the motion of the optical system in order to determine the location of the optical system at different points in time. The image processing circuitry uses the location information to appropriately combine the segments. For example, the endoscopic system may detect the motion of the optical system by sensing markers on an elongate carrier through which the optical system is passed. Alternatively, the endoscopic system directly detects the location of the optical system using one or more position sensors, as is known in the art of medical position sensing.

Alternatively or additionally, stitching techniques are used that are known in the art of panoramic image creation and processing.

This image capture and processing technique generally enables higher-resolution imaging of a large field than is possible using conventional techniques, ceteris paribus. Using conventional techniques, a relatively wide area 236 must generally be captured simultaneously in order to provide a useful image to the physician. In contrast, the techniques described herein enable the display of wide area 236 while only capturing relatively narrow image segments 222. This enables the optics of the optical system to be focused narrowly on an area of wall 230 having a width approximately equal to that of each image segment 222.

Figure 6:
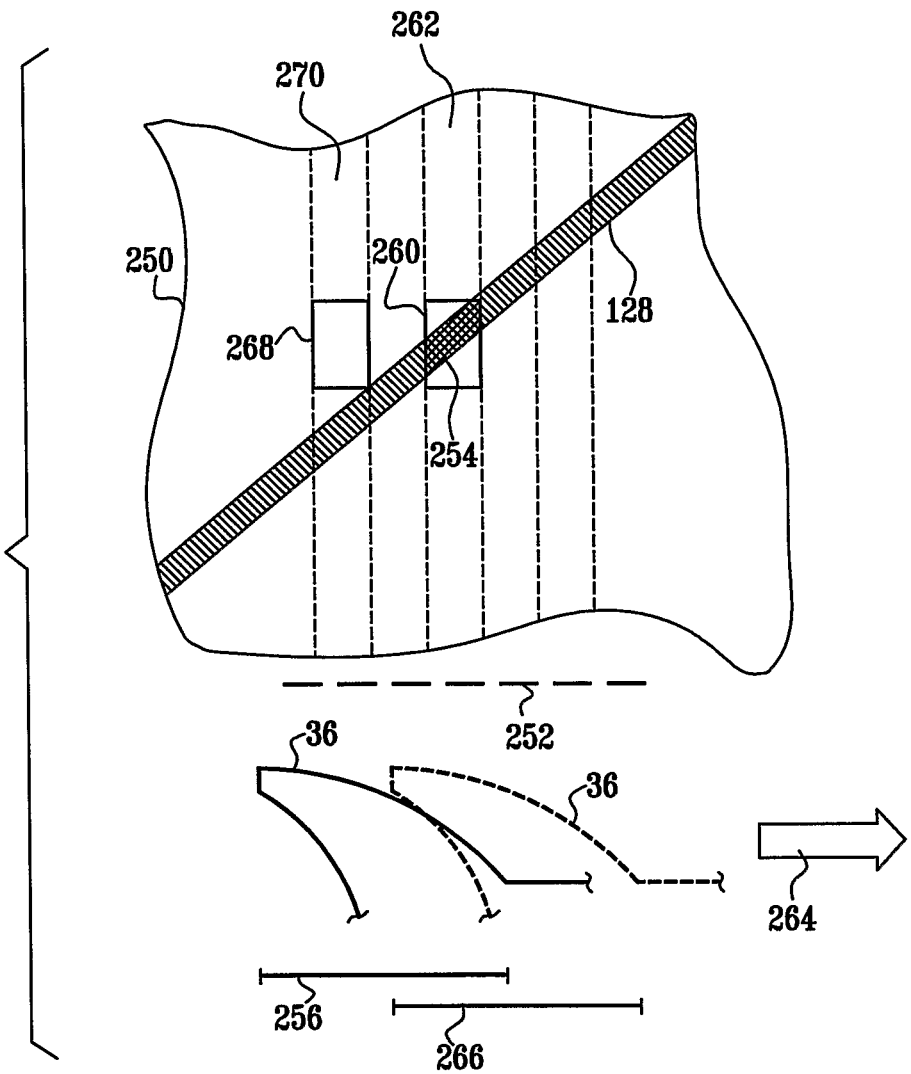
FIG. 6 is a schematic illustration of a portion of a field of view of the optical system of FIG. 1, in accordance with an embodiment of the present invention.

Reference is now made to FIG. 6, which is a schematic illustration of a portion of a field of view 250 of optical system 20, in accordance with an embodiment of the present invention. As described hereinabove with reference to FIG. 4, in an embodiment power cable 128 is oriented diagonally with respect to a rotation axis 130 of optical member 34 (a line 252 in FIG. 6 is parallel to rotation axis 130 of FIG. 4). As a result, power cable 128 blocks the fixed areas of the surface of optical member 34 over which the power cable passes, resulting in blind spots as optical system 20 is moved through the lumen of the subject.

For example, when distal portion 36 of optical member 34 is in a first position 256, an area of interest 254 in a visual area 260 of an image segment 262 is blocked. As optical system 20 is moved through the lumen, e.g., in the direction indicated by an arrow 264, distal portion 36 arrives at a second position 266. In this position, area of interest 254 is now visible in a visual area 268 of an image segment 270. For some applications, the image processing circuitry replaces the blocked image of area of interest 254, which was captured in visual area 260, with the visible image of area of interest 254, which was captured in visual area 268. In this manner, the image processing circuitry constructs a complete, unobstructed image of field of view 250.

In an embodiment of the present invention, image processing circuitry produces a stereoscopic image by capturing two images of each point of interest from two respective sequential viewpoints while the optical system is moving, e.g., through a lumen in a subject. For each set of two images, the location of the optical system is determined, such as by using the location determination techniques described hereinabove. Using this location information, the image processing software processes the two images in order to generate a stereoscopic image. Appropriate stereoscopic image processing techniques will be evident to those skilled in the art, having read the present application.

In an embodiment of the present invention, image processing circuitry converts a lateral omnidirectional image of a lumen in a subject to a two-dimensional image. Typically, the image processing circuitry longitudinally cuts the omnidirectional image, and then unrolls the omnidirectional image onto a single plane. This technique allows, for example, creation of a composite photograph of a length of the colon of a patient, seen as if the colon were opened by a longitudinal incision.

Although embodiments of the present invention have been described with respect to medical endoscopes, the techniques described herein are also applicable to other endoscopic applications, such as industrial endoscopy (e.g., pipe inspection).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an optical system for use in an endoscope, the optical system having distal and proximal ends and comprising:
    an image sensor, positioned at the proximal end of the optical system;
    a distal lens;
    a single optical member positioned between the distal lens and the image sensor, the optical member being transparent and having distal and proximal ends, said distal end having a curved surface facing said distal lens, a distal indentation at the curved surface of the distal end of the optical member, and a lateral surface, at least a distal portion of which is curved, said lateral surface being configured to receive lateral light to provide omnidirectional lateral viewing; and
    a convex mirror having a surface covered by a non-transparent reflective coating, positioned between the distal lens and the optical member and being coupled to the distal end of the optical member for reflecting the lateral light into the optical member, and shaped so as to define an opening through which distal light arriving from a forward direction passes,
    the optical member and the convex mirror are concentric about a common rotation axis, and
    the opening in the convex mirror provides passage for the distal light onto a proximal surface of the distal indentation, said proximal surface being spaced from and indented from said curved surface and configured as a lens that focuses said distal light passing therethrough, such that said distal light and said lateral tight travel inside the optical member through separate, non-overlapping optical paths.

2. The apparatus according to claim 1, wherein the optical system comprises one or more proximal lenses, positioned between the optical member and the image sensor.

3. The apparatus according to claim 1, wherein the convex mirror is substantially hyperbolic.

4. The apparatus according to claim 1, wherein the indented refracting surface is concave.

5. The apparatus according to claim 1, further comprising at least one light source configured to illuminate a lumen in which the endoscope is placed.

6. The apparatus according to claim 5, further comprising a power cable coupled to the light source and positioned diagonally with respect to the common rotation axis, along a portion of the curved distal portion of the lateral surface of the optical member.

7. The apparatus according to claim 5, wherein the light source comprises a plurality of LEDs.

8. The apparatus according to claim 7, wherein the optical system is configured to provide distal viewing of a distal view, and wherein at least a portion of the plurality of LEDs are configured to illuminate the distal view.

9. The apparatus according to claim 7, wherein at least a portion of the plurality of LEDs are configured to illuminate laterally, in order to provide illumination for the omnidirectional lateral view.

10. The apparatus according to claim 5, wherein the light source is configured to be disposed at a remote site with respect to the optical system, and wherein the apparatus further comprises at least one optical fiber configured to convey light from the light source.

11. The apparatus according to claim 1, further comprising a distal lens positioned distal to the convex mirror.

12. The apparatus according to claim 11, wherein an axis of the distal lens is the common rotation axis.

13. The apparatus according to claim 1, wherein the indented refracting surface at the proximal end, of the optical member is configured to transmit light from the omnidirectional lateral view.

14. The apparatus according to claim 13, wherein the optical system is configured to provide a distal image of a distal view, and wherein the indented refracting surface at the proximal end of the optical member is configured to transmit light from the distal view.

* * * * *